(12) United States Patent     (10) Patent No.: US 8,801,652 B2
Landherr et al.     (45) Date of Patent: *Aug. 12, 2014

(54) EARLY STAGE PERITONITIS DETECTION APPARATUS AND METHODS

(75) Inventors: Frank J. Landherr, Cary, IL (US); Lynn E. Jensen, Syracuse, UT (US); Jay M. Lan, Thousand Oaks, CA (US)

(73) Assignee: Fresenius Medical Care Holding, Inc., Waltham, MA (US)

( * ) Notice: Subject to any disclaimer, the term of this patent is extended or adjusted under 35 U.S.C. 154(b) by 1588 days.

This patent is subject to a terminal disclaimer.

(21) Appl. No.: 11/880,656

(22) Filed: Jul. 23, 2007

(65) Prior Publication Data

US 2008/0045884 A1    Feb. 21, 2008

Related U.S. Application Data

(60) Provisional application No. 60/833,763, filed on Jul. 27, 2006.

(51) Int. Cl.
*A61M 1/00* (2006.01)
*G06F 19/00* (2011.01)
*B01D 61/00* (2006.01)

(52) U.S. Cl.
USPC .................. 604/29; 604/19; 604/27; 702/19; 210/645

(58) Field of Classification Search
None
See application file for complete search history.

(56) References Cited

U.S. PATENT DOCUMENTS

| | | | |
|---|---|---|---|
| 4,279,509 A | 7/1981 | Daffern | |
| 5,007,732 A | 4/1991 | Ohki et al. | |
| 5,025,523 A | 6/1991 | Zappa et al. | |
| 5,304,173 A | 4/1994 | Kittrell et al. | |
| 5,383,199 A | 1/1995 | Laudenslager et al. | |
| 5,690,813 A | 11/1997 | Coale | |
| 6,067,157 A | 5/2000 | Altendorf | |
| 6,228,047 B1 | 5/2001 | Dadson | |
| 2003/0044853 A1 | 3/2003 | Socks et al. | |
| 2003/0059370 A1 | 3/2003 | Quijano et al. | |
| 2005/0139515 A1 | 6/2005 | Gu et al. | |
| 2005/0213425 A1 | 9/2005 | Wang et al. | |
| 2006/0154642 A1 | 7/2006 | Scannell | |
| 2007/0020341 A1 | 1/2007 | Miyata | |
| 2008/0015487 A1 | 1/2008 | Szamosfalvi et al. | |
| 2008/0045884 A1 | 2/2008 | Landherr et al. | |
| 2008/0183126 A1 | 7/2008 | Landherr et al. | |
| 2008/0183127 A1 | 7/2008 | Landherr et al. | |

FOREIGN PATENT DOCUMENTS

| | | | |
|---|---|---|---|
| JP | 08-098882 A | 4/1996 | |
| JP | 08-107890 A | 4/1996 | |
| JP | 8089571 | 4/1996 | |
| JP | 09-210995 A | 8/1997 | |
| JP | 09-239023 A | 9/1997 | |
| JP | 2001-509888 A | 7/2001 | |
| JP | 2001-511400 A | 8/2001 | |
| JP | 2003-501155 A | 1/2003 | |
| JP | 2006-149938 A | 6/2006 | |
| JP | 2011-510324 A | 3/2011 | |
| WO | 01/17422 A1 | 3/2001 | |
| WO | 2004/093669 A1 | 11/2004 | |

OTHER PUBLICATIONS

Penders et a. (Nephrol. Dial. Transplant. (2004) vol. 19, pp. 463-468).*
Leary et al. (Journal of Histochemistry and Cytochemistry (1979) vol. 27, pp. 315-320).*
Terstappen et al. (Cytometry (1988) vol. 9, pp. 39-43).*
Chow et al. (Clin. J. Am. Soc. Nephro. (2006) vol. 1, pp. 768-773—published Jul. 1, 2006 and published online prior to Jul. 1, 2006).*
Ellis et al., Metabolic fingerprinting in disease diagnosis: biomedical applications of infrared and Raman spectroscopy. Analyst. Aug. 2006;131(8):875-85. Epub Apr. 25, 2006.
Keane WF, Alexander SR, Bailie GR, Boeschoten E, Gokal R, Golper TA, Holmes CJ, Huang CC, Kawaguchi Y, Piraino B, Riella M, Schaefer F, Vas S. Peritoneal dialysis-related peritonitis treatment recommendations: 1996 update. Perit Dial Int. Nov.-Dec. 1996;16(6):557-73.
Japanese Office Action issued Feb. 24, 2012 for Application No. 2010-544287.
Zinn et al., Laminar flow chamber for continuous monitoring of biofilm formation and succession. Methods Enzymol. 1999;310:224-32.
International Search Report, International Application No. PCT/US08/52056, Mailed Aug. 1, 2008.
International Search Report, International Application No. PCT/US08/52062, Mailed Jul. 25, 2008.
Sharma. Evaluation of fiberoptic-based systems for measurement of optical properties in highly attenuating turbid media. Biomed Eng Online. Aug. 23, 2006, 5(49):1-14.
Baena et al., Raman spectroscopy in chemical bioanalysis. Curr Opin Chem Biol. Oct. 2004;8(5):534-9.
Japanese Office Action issued Oct. 19, 2012 for Application No. 2010-544288 (7 Pages).

(Continued)

*Primary Examiner* — Lori A Clow
(74) *Attorney, Agent, or Firm* — Nutter McClennen & Fish LLP; David J. Powsner (57) ABSTRACT

The invention provides, inter alia, automated medical methods and apparatus that test PD effluent in a flow path (e.g., with an APD system or CAPD setup) to detect, for example, the onset of peritonitis, based on optical characteristics of the effluent resolved at cellular scales of distance. For example, according to one aspect of the invention, an APD machine includes, in an effluent flow path, apparatus for early stage peritonitis detection comprising an illumination source and a detector. The source is arranged to illuminate peritoneal effluent in a chamber that forms part of the flow path, and the detector is arranged to detect illuminant scattered by the effluent. The detector detects that reflected or scattered illuminant at a cellular scale of resolution, e.g., on a scale such that separate cellular-sized biological (or other) components in the effluent can be distinguished from one another based on scattering events detected by the detector.

61 Claims, 6 Drawing Sheets

(56) References Cited

OTHER PUBLICATIONS

Canadian Office Action for Application No. 2594634, issued Oct. 22, 2013 (4 pages).

James J. Bohning et al. The Raman Effect published Dec. 15, 1998 by the American Chemical Society for short overview of Raman Spectroscopy.

* cited by examiner

FIG. 5C

EARLY STAGE PERITONITIS DETECTION APPARATUS AND METHODS

This application claims the benefit of U.S. Provisional Patent Application Ser. No. 60/833,763, filed Jul. 27, 2006, entitled "Early Stage Peritonitis Detection Apparatus and Methods," the teachings of which are incorporated herein by reference.

BACKGROUND OF THE INVENTION

The invention relates to apparatus and methods for medical diagnostic testing. It has application, inter alia, in detecting the onsite of peritonitis, for example, during continuous ambulatory peritoneal dialysis (CAPD) and automated peritoneal dialysis (APD) procedures.

Peritoneal dialysis (PD) is a medical procedure for removing toxins from the blood that takes advantage of the semipermeable membrane surrounding the walls of the abdomen or peritoneal cavity. During a PD procedure, a solution is introduced into the patient's abdomen, where it remains for up to several hours, removing blood toxins via osmotic transfer through that membrane. At completion of the procedure, the solution is drained from the body along with the toxins. CAPD is the manual form of this procedure, requiring that the patient manually drain fresh PD solution into, and spent PD solution out from, the peritoneum. In APD, the entire procedure is handled by automated equipment.

Peritonitis is a common complication of both CAPD and APD. Often caused by introduction of bacteria (e.g., from the tubing, connectors and other apparatus that make up the PD transfer set) to the peritoneum during dialysis, this swelling of the peritoneum can cause vomiting, abdominal tenderness and a host of other symptoms. Although responsive to antibiotics, peritonitis can end a patient's ability to stay on APD and CAPD therapies. In extreme cases, it can be fatal.

Standard tests for peritonitis, usually conducted on occurrence of acute clinical symptoms, include the Gram stain procedure, performing a cell count on the peritoneal fluid, culturing that fluid, and/or performing a blood culture. Largely, these tests can only be done in the lab, after a patient has presented with symptoms. By that time, the peritonitis may well have set in, resulting in undue patient distress and potentially necessitating more extensive treatment.

More recently, reagent test strips have become available, making it possible for physicians or patient's themselves to perform more immediate diagnosis. However, test strips have a limited time window of utility and have generally not been successful in early stage detection.

CAPD and APD patients are typically counseled to maintain a keen eye for another symptom of peritonitis: a turbid or cloudy effluent bag. This can be late-developing, unfortunately, and is further compounded if the PD solution remains in the body for a long period before expulsion (as is the case, for example, during daytime dwells of APD patients). Detection of turbid effluent is further complicated in APD equipment with long drain lines, since patients may only see the effluent lines and not the effluent bag (where the turbidity is more readily apparent). Moreover, patients who are blind or have poor eyesight must rely on friends, family and/or caregivers to inspect the spent PD fluid for turbidity.

The prior art suggests that such cloudiness might be detected automatically, e.g., within APD equipment, by detecting the overall amount of non-coherent, polychromatic light that passes through a vessel of PD effluent by use of a source of such light positioned on one side of the vessel and a detector positioned at an opposing side. Implementations of this technique have generally not proven reliable because of poor signal-to-noise.

An object of the invention is to provide improved methods and apparatus for medical diagnosis, testing and/or treatment in the home or lab.

A further object of the invention is to provide improved methods and apparatus for PD therapy.

A still further object of the invention is to provide improved methods and apparatus for detecting the onset of peritonitis, e.g., in connection with peritoneal dialysis.

Yet a still further object of the invention is to provide such methods and apparatus as can be implemented at reasonable cost, yet, produce efficacious results.

SUMMARY OF THE INVENTION

The foregoing are among the objects attained by the invention which provides, in one aspect, automated medical testing methods and apparatus that detect the onset of peritonitis from optical characteristics of PD effluent resolved at cellular scales in the flow path.

For example, according to one aspect of the invention, an APD machine includes, in an effluent flow path, apparatus for early stage peritonitis detection comprising an illumination source and a detector. The source is arranged to illuminate peritoneal effluent in a chamber that forms part of the flow path, and the detector is arranged to detect illuminant scattered by the effluent. The detector detects that scattered illuminant at a cellular scale of resolution, e.g., on a scale such that separate cellular-sized biological (or other) components in the effluent can be distinguished from one another based on scattering events detected by the detector.

Related aspects of the invention provide apparatus as described above in which the detector is arranged such that separate white blood cells (WBCs) in the effluent can be distinguished from one another based on reflection and scattering (collectively, "scattering") of illuminant. Apparatus with a detector so arranged can, by way of example, count such WBCs from scattering and can, further, signal the onset of peritonitis if those counts change over time and/or vary from a baseline.

Further related aspects of the invention provide apparatus as described above in which the detector is arranged such that cellular-sized biological (or other) components of different types in the effluent can be distinguished based on illuminant scattered by them. Related aspects of the invention provide such apparatus in which the detector is so arranged as to permit WBCs in the effluent to be distinguished based on scattering from red blood cells (RBCs), fibrin and/or other components.

Other aspects of the invention provide apparatus as described above which signal the onset of peritonitis based on variance, e.g., over time and/or from a baseline, in counts of selected biological components in the effluent. Related aspects of the invention provide such apparatus as compute a trend of variance of those counts, e.g., with respect to WBCs in the effluent. Further related aspects of the invention provide such apparatus which compute that trend as a slope of a curve of those counts with respect to time and that signals the onset of peritonitis when that slope exceeds a selected amount.

Other related aspects of the invention provide such apparatus in which the detector counts scattering events—i.e., events in which illuminant is reflected and scattered from the effluent to the detector—based on intensity and/or location of the scattering event. In one such aspect of the invention, the detector comprises a pin diode that is configured to count scattering events, e.g., based on the intensity of illuminant detected from the effluent. An apparatus according to this aspect of the invention can, for example, signal the onset of peritonitis when the number of counts of a certain intensity (or range of intensities, e.g., which are based on cell size) varies, e.g., from a baseline and/or among drains of spent PD solution from the patient, and/or when a trend of that variance over time exceeds a selected amount.

In other such aspects, the detector comprises a charge-coupled device (CCD) that is arranged to image the chamber—that is, to record scattering events based on both location and (cumulative) intensity. Further related aspects of the invention provide such apparatus in which the detector generates a histogram of one or more such images, counting scattering events (e.g., based on intensity). Still further related aspects of the invention provide such apparatus which generates a histogram from multiple images taken, for example, during a drain of spent PD solution from the patient. As above, apparatus according to these aspects of the invention can, for example, signal the onset of peritonitis when the number of counts of a certain intensity (or range of intensities) varies over time, e.g., from a baseline and/or among successive drains of PD effluent from the patient.

Other related aspects of the invention provide such apparatus which the histograms are performed only with respect to selected scattering events recorded in the images, e.g., scattering events of selected intensities and/or lengths. Apparatus accord to these aspects of the invention can, for example, signal the onset of peritonitis when the number of counts from scattering events likely caused by WBCs (and not, for example, RBCs or fibrin) vary over time from a baseline and/or among successive drains of PD effluent from the patient.

Further aspects of the invention provide such apparatus in which the illumination source is a laser diode (or other source of coherent illuminant).

Related aspects of the invention provide such apparatus in which the detector is arranged to detect side-scattering events, e.g., events detectable within a field of view perpendicular to a ray of illuminant sourced by the laser diode.

Further related aspects of the invention provide such apparatus in which illuminant sourced by the laser diode comprises a beam disposed—and, specifically, for example, centered—within a portion of the flow path from which scattering events are counted by the detector.

Still further related aspects of the invention provide such apparatus in which illuminant sourced by the laser has a beam width selected based on size characteristics of the biological (or other) components from which scattering events are to be counted. Further related aspects of the invention provide such methods in which the beam width has a diameter of about 1.5 times a size of components, e.g., WBCs. Yet still other aspects of the invention provide such apparatus in which the beam width has any of a circular and gaussian cross-section, or other beam size and/or shape.

Further aspects of the invention provide such apparatus in which the detector comprises a lens arranged to resolve illuminant scattered from components of the effluent at a cellular scale of distances. Related aspects of the invention provide such apparatus in which the lens is arranged to provide a depth of field encompassing a substantive portion of the flow path within the detector field of view, e.g., a depth of field that encompasses a flow chamber from which scattering events are detected.

Other aspects of the invention provide apparatus as described above for use in connection with CAPD procedures.

Still other aspects of the invention provide such apparatus for use in detecting the on-set of peritonitis in fluid flows established independent of APD and/or CAPD equipment in which the PD fluid is collected. Such apparatus has application, for example, in testing bags (or other collections) of spent PD effluent, e.g., as they are being emptied for disposal or for further testing.

Yet still other aspects of the invention provide PD kits that include, in addition to conventional components (such as tubing, clamps, sterilization wipes, and so forth), a test apparatus as described above.

Still yet other aspects of the invention provide methods of testing PD effluent for the onset of peritonitis paralleling the operations described above.

Yet still other aspects of the invention provide apparatus and methods as described above for use in detecting, in a PD effluent flow, blood (RBCs), bubbles and other undesirable byproducts of CAPD, APD and so forth. A related aspect of the invention is to provide such apparatus and methods for use in hemodialysis and other medical procedures

BRIEF DESCRIPTION OF THE DRAWINGS

A more complete understanding of the invention may be attained by reference to the drawings, in which.

DETAILED DESCRIPTION OF THE ILLUSTRATED EMBODIMENT

Figure 1A:
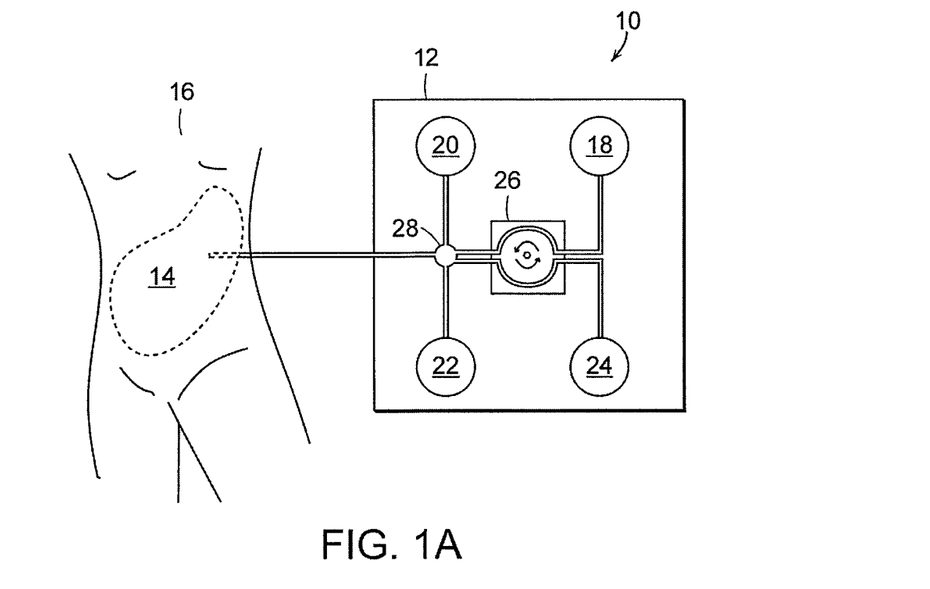
FIGS. 1A-1E depict an automated peritoneal dialysis (APD) treatment system according to one practice of the invention and of the type with which the invention can be practiced.

FIG. 1A depicts an automated peritoneal dialysis (APD) treatment system 10 according to one practice of the invention and of the type with which the invention can be practiced. The system 10 includes a cycler 12 or other apparatus to facilitate introducing fresh peritoneal dialysis (PD) solution into, and removing spent PD solution from, the peritoneum 14 of a patient 16.

The system 10 includes a PD solution supply chamber 18, a heating chamber 20, a weigh chamber 22, and a disposal chamber 24, all constructed an operated in the conventional manner known in the art (albeit as adapted for inclusion of PD effluent test apparatus as discussed elsewhere herein). Thus, PD supply chamber 18 holds a supply of fresh PD solution for delivery to the patient 16; heating chamber 20 brings the fresh PD solution to an appropriate temperature for delivery to the peritoneum; weigh chamber 22 hold spent PD solution expelled from the peritoneum, e.g., for weighing; and, disposal chamber 24 holds spent PD solution for disposal.

Figure 1B:
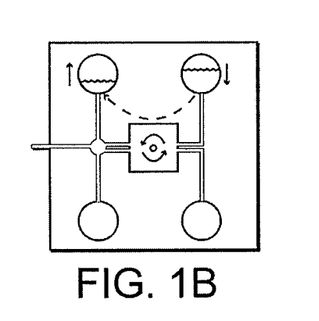
Figure 1C:
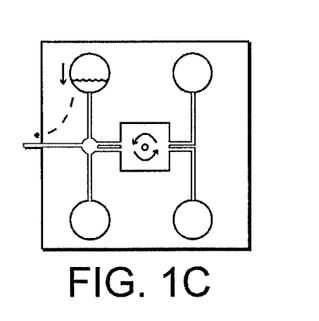

Pump 26 operates under control of a micro-controller (not shown) to move solution between the chambers 18-24 in the conventional manner, e.g., as illustrated in FIGS. 1B-1E. Thus, for example, as shown in FIG. 1B, pump 26 moves fresh PD solution from supply chamber 18 to heating chamber 20 so that the latter can bring that solution to temperature, prior to its introduction into the patient's peritoneum 14. Once the desired temperature is achieved and treatment is to begin, the pump 26 opens a valve 28, allowing the heated, fresh PD solution to flow via gravity-assist into the peritoneum 14. See, FIG. 1C.

Figure 1D:
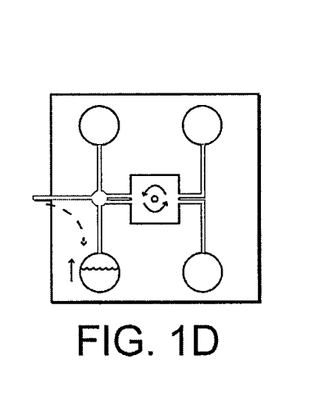
Figure 1E:
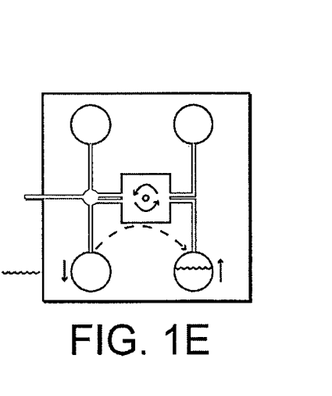

Per FIG. 1D, once the PD has dwelled for the desired period of time in the peritoneum 14, pump 26 opens valve 28 so that the spent PD solution can flow into chamber 22 for weighing (e.g., to insure that sufficient solution has be removed from the peritoneum 14), as per convention in the art. Pump 26 then moves the spent effluent from the weigh chamber 22 to the disposal chamber 24 for collection prior to disposal by the patient, health care worker, or otherwise. See, FIG. 1D.

The conventional aspects of system 10 shown and described here are merely by way of example. It will be appreciated that apparatus for testing PD effluent (as discussed elsewhere herein) may be used in connection with APD equipment of other configurations and modes of operation than those shown in FIGS. 1A-1E and described above.

Figure 2A:
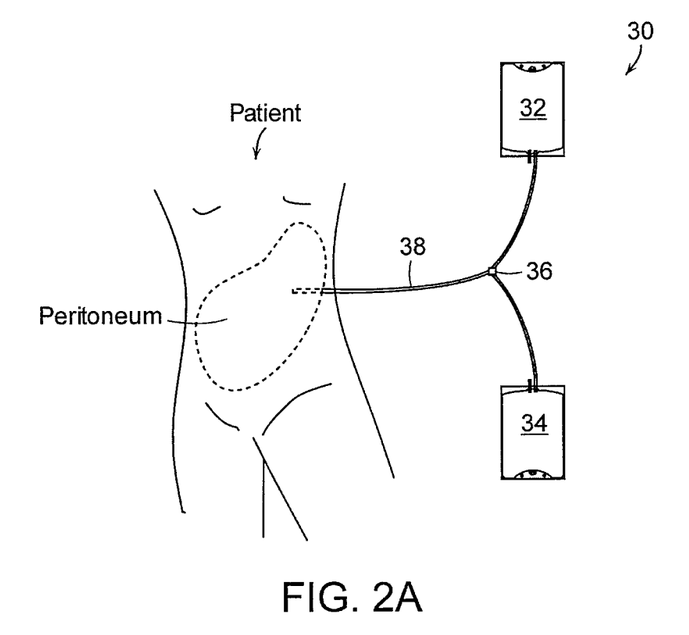
FIGS. 2A-2C depict a continuous ambulatory peritoneal dialysis (CAPD) treatment system according to one practice of the invention and of the type with which the invention can be practiced.
Figure 2B:
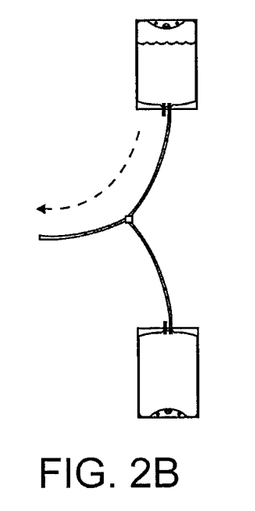
Figure 2C:
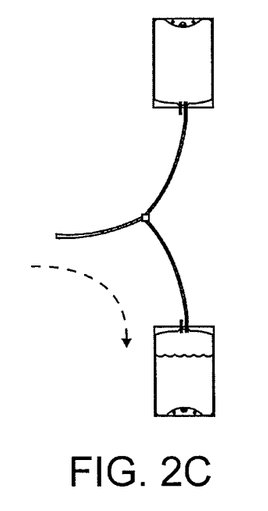

FIG. 2A depicts a continuous peritoneal dialysis (CAPD) treatment system 30 according to one practice of the invention and of the type with which the invention can be practiced. The system 30 includes a fresh PD solution supply bag 32, a spent PD solution bag 34, and a y-connector 36 for coupling those bags to peritoneal transfer set 38. The system 30 is constructed and operated in the conventional manner known in the art (albeit as adapted for inclusion of PD effluent test apparatus as discussed elsewhere herein). Thus, for example, the patient connects bags 32, 34 to the y-connector 36, as shown in FIG. 2B, for a brief sterilizing flush of the connector 36. Then, as further shown in that drawing, the patient configures the connector 36 to permit fresh PD solution to flow, under gravity assist, from bag 32 into the peritoneum. Once the PD solution has dwelled for the desired period, the patient reconfigures the connector 36 to permit the spent PD solution to drain to bag 34 for disposal. See, FIG. 2C.

The conventional aspects of system 30 shown and described here are merely by way of example. It will be appreciated that apparatus for testing PD effluent (as discussed elsewhere herein) may be used in connection with CAPD equipment of other configurations (e.g., with straight transfer tubing sets) and modes of operation than those shown in FIGS. 2A-2C and described above.

Figure 3:
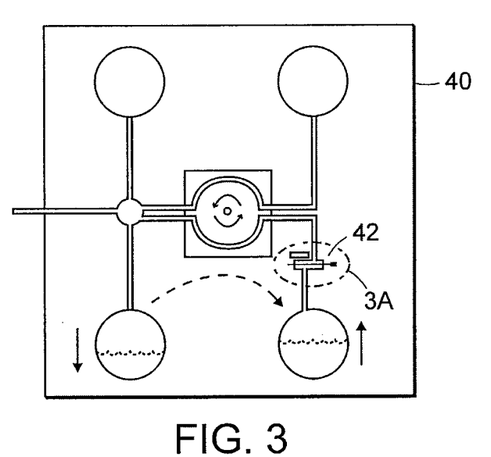
FIGS. 3A-3B depict apparatus for testing PD effluent according to one practice of the invention.
Figure 3A:
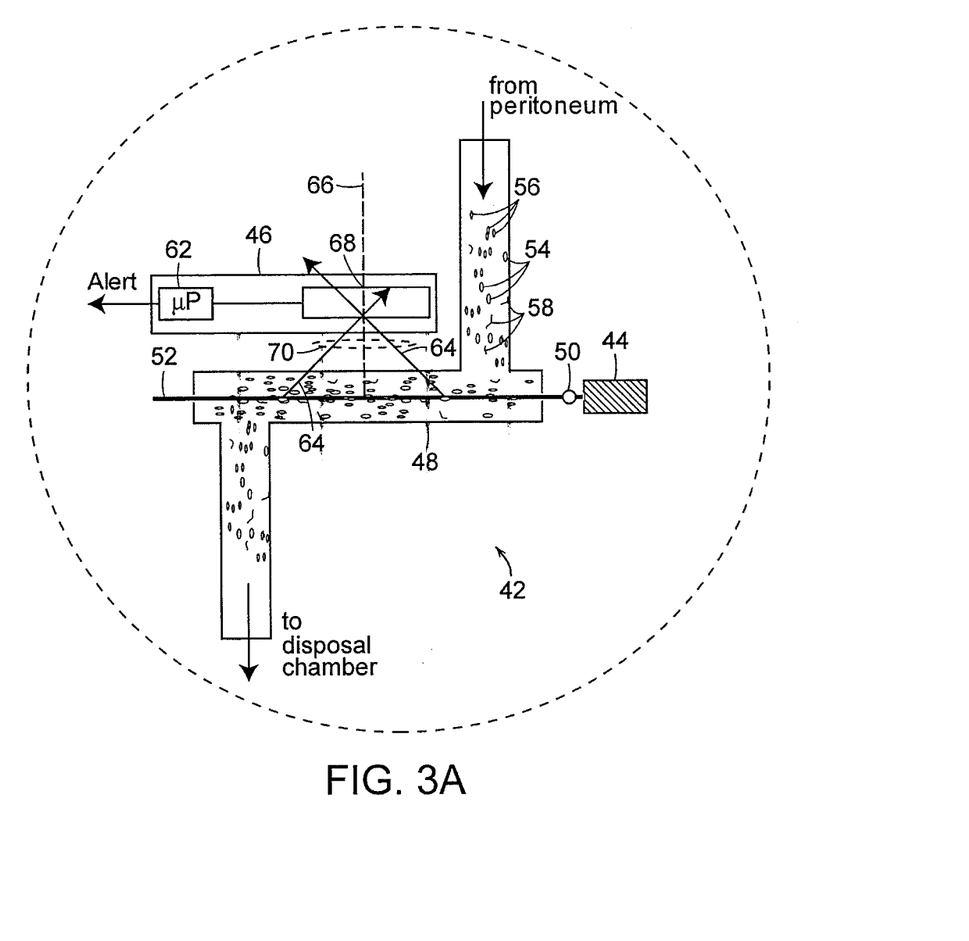
Figure 3B:
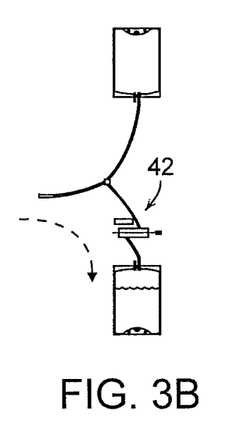

FIG. 3A depicts an APD cycler 40 that is constructed and operated in the manner of cycler 12 (FIG. 1), albeit including apparatus 42 according to the invention for testing PD effluent (i.e., PD solution drained from the peritoneum) in a flow path of cycler 40 and/or other APD system or components of which it is a part. The cycler 40 (with test apparatus 42) can be used in place of cycler 12 in the system 10 (FIG. 1), as well as in other APD treatment systems. Likewise, the test apparatus 42 can be coupled into the effluent flow path (i.e., drain lines) of the system 30 (FIG. 2), as graphically depicted in inset FIG. 3B, as well as in other CAPD systems. Moreover, the apparatus can be combined with kits for APD and CAPD procedures (e.g., kits that include tubing, clamps, sterilization wipes and so forth). Still further, the apparatus 42 can be coupled into fluid flow paths of laboratory, doctor's office, hospital or home test equipment and it can be sold with kits for such testing (e.g., kits that include PD effluent sample phials, drop boxes, labeling and so forth). For convenience, operation of test apparatus 42 will be described with respect to cycler 40 of FIG. 3A, though, it will be appreciated that apparatus 42 can be configured and operated similarly in the aforementioned and other environments in which it is used.

By way of overview, illustrated apparatus 42 tests PD effluent in a flow path—here, the path from peritoneum 14 to disposal chamber 24—for the onset of peritonitis and/or other conditions (e.g., the presence of blood and/or bubbles). To this end, that apparatus includes an illumination source 44 and a detector 46. The source 44 is arranged to illuminate peritoneal effluent in a chamber 48 that forms part of the flow path, and the detector 46 is arranged to detect illuminant scattered by that effluent, e.g., in a direction normal to the illuminant beam.

The source 44 and detector 46 are configured so that the detector detects reflected and/or scattered (collectively, "scattered") illuminant at a cellular scale of resolution, e.g., on a scale such that separate cellular-sized biological (or other) components in the effluent can be distinguished from one another. In applications such as those to which the illustrated embodiment is directed, i.e., early detection of the onset of peritonitis, this permits separate white blood cells (WBCs) in the effluent to be distinguished from one another (as well as from red blood cells, fibrin and other components of the effluent) so that they can be counted and so that the rate of change of those counts can be measured for purposes of detecting and signaling the onset of peritonitis. In other embodiments, this permits red blood cells (or other components, such as bubbles) in the effluent to be distinguished from one another (as well as from WBCs, fibrin, etc.) and counted; and so forth.

As noted, detector 46 is configured to detect illuminant scattered from the chamber 48 at a cellular scale of resolution, e.g., on a scale such that separate cellular-sized components in the effluent can be distinguished from one another. As further noted, in the illustrated embodiment, this permits separate WBCs 54 in the effluent to be distinguished from one another (as well as from red blood cells 56, fibrin 58 and other components of the effluent) so that they can be counted and so that the rate of change of those counts can be measured for purposes of detecting and signaling the onset of peritonitis. In other embodiments, this permits other components—such as RBCs 56, fibrin 58, etc.—to be detected in the effluent for purposes signaling other conditions.

The illumination source of the illustrated embodiment comprises a low-power laser diode generating a monochromatic collimated beam. Here, the wavelength is selected at 630 nm to coincide with an optical sensitivity of detector 46 and for suitability in reflection and scattering (collectively, as above, "scattering") from at least selected components (e.g., white blood cells) in the effluent. Other embodiments may utilize lasers of other wavelengths, monochromatic or otherwise, selected in accord with foregoing or other criterion, e.g., 830 nm and 780 nm lasers, to name but a few, as well as other illumination sources, monochromatic, polychromatic, coherent and/or otherwise.

The collimated beam generated by laser diode 44 of the illustrated embodiment is optionally shaped by lens or columinator 50 to result in a beam 52 of gaussian or circular cross-section, though beams of other shapes may be used in other embodiments.

Lens 52 shapes the beam to optimize scattering from at least selected components in the effluent. In the illustrated embodiment, this means sizing the beam at 1×-2× and, preferably, about 1.5× the average size of the effluent components to be preferentially be detected—here, WBCs. Given an average size of 12-15 µm for neutrophils and eosinophils, 8-10 µm for lymphocytes, and 16-20 µm for monocytes, beam 52 of the illustrated embodiment is accordingly sized between 10-40 μm and, preferably, 15-25 μm and, still more preferably, about 20 μm. This optimizes the apparatus 42 for preferential detection of WBCs over, for example, red blood cells 56, fibrin 58 and other components of the PD effluent. Other embodiments may use other beam sizes, e.g., for reason of preferential detection of other effluent components or otherwise.

The beam 52 of the illustrated embodiment is aimed to pass through chamber 48 in order to illuminate the effluent therein for purposes of evoking scattering from biological (and other) components in that fluid. Although in the illustrated embodiment, the beam is aimed to pass through a center of the chamber 48, as shown, in other embodiments the beam 52 may be directed otherwise.

Turning back to FIG. 3A, detector 46 detects and counts scattering events—i.e., events in which illuminant is scattered from the effluent in the chamber 48 to the detector 46—based on the intensity and/or location of those events. In the illustrated embodiment, the detector 46 is, particularly, arranged to detect side-scattering, e.g., events within a field of view 64 centered on an axis 66 that is normal to the beam 52, as shown. In other embodiments, the detector may be arranged to detect other scattering events, e.g., back-scattering, forward-scattering, side-scattering at angles β other than normal. Thus, while in the illustrated embodiment, β is substantially 90°, more generally, β is in the range 30°-150°; more preferably, between, 60°-120°; still more preferably, between 80°-100°; and, still more preferably, substantially 90°, as illustrated.

In some embodiments, the detector 46 employs a single-cell (or few-celled) photo diode, i.e., pin-diode 68, for purposes of detecting and signaling the occurrence of such scattering events. A lens 70 facilitates focusing the diode so that it detects those events at a cellular scale of resolution, e.g., on a scale such that separate cellular-sized biological (or other) components in the effluent can be distinguished (based on such scattering) from one another. In the illustrated embodiment, lens 70 is selected and arranged (vis-a-vis chamber 48 and diode 68) to preferentially focus WBCs, though, in other embodiments, the lens 70 may be focused otherwise. The lens 70 is further selected and arranged for a desired depth of focus within the field of view 64, e.g., in the illustrated embodiment, a depth of focus matching the depth of compartment 48, or a substantial portion thereof. The chamber 48 is configured to match the laser beam size and shape, e.g., so as to minimize or wholly avoid reflections (or scattering) of the beam 52 off the inner walls of the chamber itself.

The laser diode 68 is selected and/or otherwise configured (e.g., through use of appropriate circuitry) to detect scattering from selected components of the effluent—here, preferentially, WBCs, though, in other embodiments, RBCs, fibrin, bubbles other components of the effluent. Regardless, such selection and/or configuration can be performed empirically (e.g., by testing scattering detected from an effluent of known composition) or otherwise.

Scattering events detected and signaled by the diode 60 are routed to a microprocessor 62 (or other suitable element) for analysis. In the illustrated embodiment, this comprises counting events signaled over time and generating an alert, e.g., when the number of counts of a certain intensity (or range of intensities) varies, e.g., (i) from a baseline established for patient 16, (ii) among successive drains of spent PD solution from that patient 16, and/or (iii) when a trend of that variance over time—and, more particularly, a rate of change of counts over time (i.e., a "critical slope")—exceeds a selected amount. Such an alert can be in the form of a visible and/or audible signal to the patient 16, health-care worker, or otherwise; a hardware or other interrupt to system 12 of which test apparatus 42 forms a part; a software function call to such system; or otherwise.

Other embodiments of the invention employ a charge-coupled device (CCD), in place of pin-diode 68, for purposes of detecting and signaling the occurrence of scattering events. As above, lens 70 facilitates focusing the CCD (and obtaining a desired depth of focus) so that it detects those events at a cellular scale of resolution and, in the illustrated embodiment, so that it preferentially focuses WBCs—though, in other embodiments, the lens 70 may be focused otherwise. In the discussion that follows, elemental designation 68 is used for the CCD, as it was for the pin-diode, since the CCD is disposed in the same functional place in apparatus 42.

As with the pin-diode, the CCD 68 is selected and/or otherwise configured to facilitate detection of scattering from selected components of the effluent (again, here, preferentially, WBCs). In this regard, the CCD 68 images the illuminated chamber 48, recording both the positions and intensities of scattering events (again, at a cellular scale of resolution) so that at least selected components (e.g., WBCs) in the effluent can be distinguished from one another and from other components of the effluent.

Figure 4:
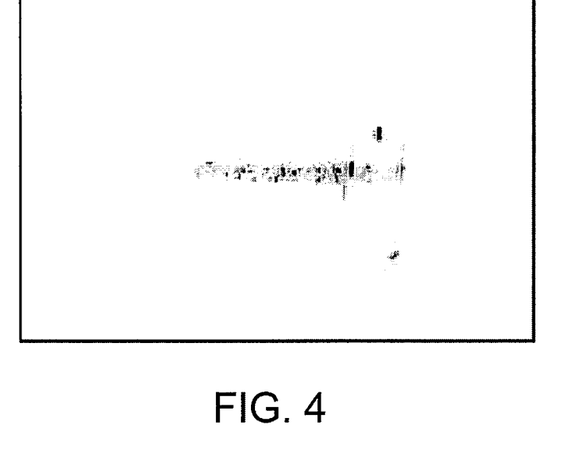
FIG. 4 depicts an image of the type generated by a charge coupled device in an apparatus according to one practice of the invention.

FIG. 4 depicts such an image—here, generated from a simulated effluent incorporating, in lieu of WBCs, 80 glass beads (sized between 10-30 microns) per μL.

Images generated by the CCD are routed to the microprocessor 62 (or other suitable element) for analysis. In the illustrated embodiment, this comprises taking a histogram of each image—or, more preferably, from multiple such images generated during drainage of spent PD solution following a single PD treatment session—with binning that is based on intensity. Depending on the number of counts in selected one(s) of the histogram bins, the microprocessor 62 can generate an alert, e.g., as discussed below.

Figure 5A:
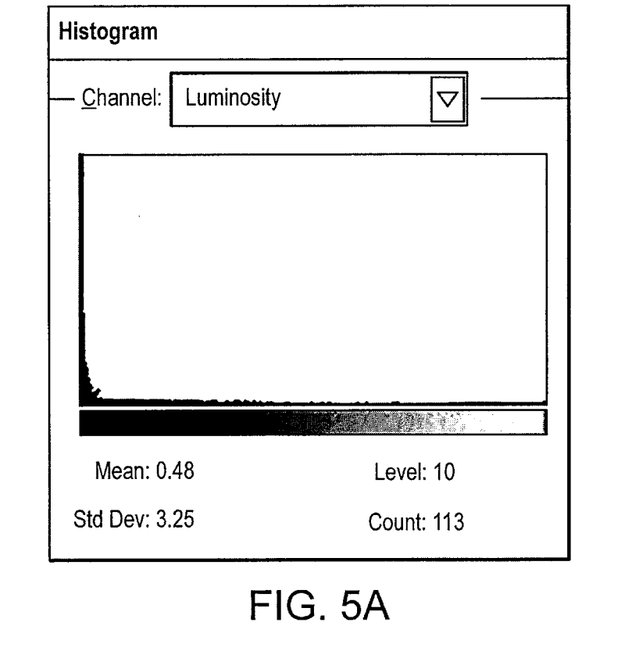
FIGS. 5A-5C depict histograms of the type generated from images generated by charge coupled devices used in practice of the invention.
Figure 5B:
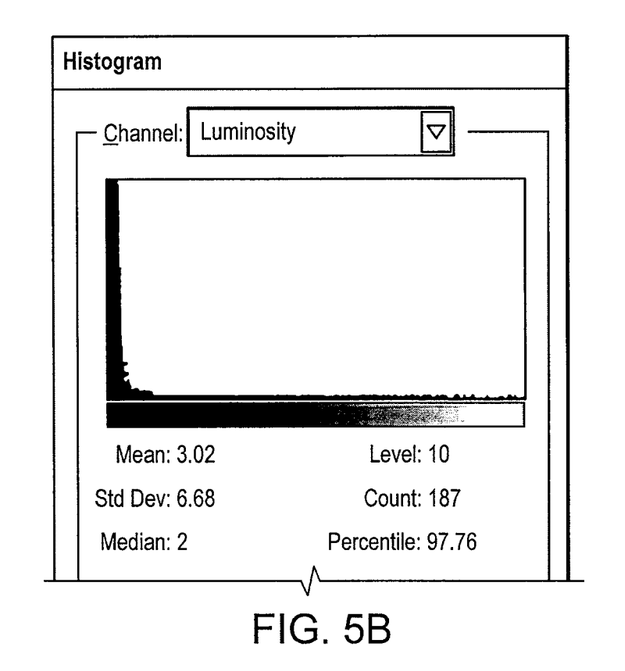
Figure 5C:
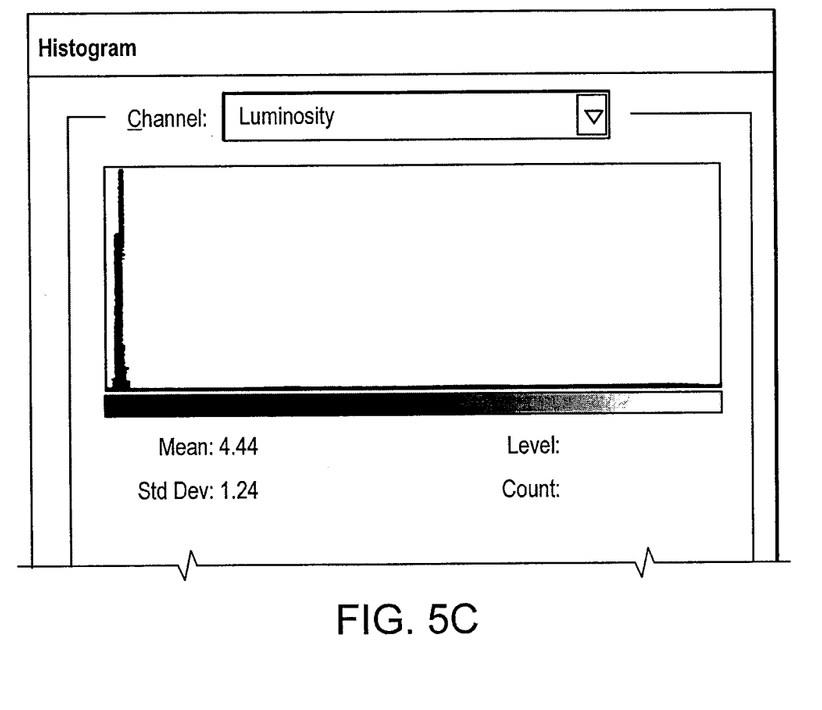

FIGS. 5A-5C depict such histograms—here, generated from a simulated effluent as described above with, respectively, 40 (FIG. 5A), 80 (FIG. 5B) and zero (FIG. 5C), glass beads per μL.

In the illustrated embodiment, it generates that alert, e.g., when the number of counts of a certain intensity (or range of intensities) varies, e.g., (i) from a baseline established for patient 16, (ii) among successive drains of spent PD solution from that patient 16, and/or (iii) when a trend of that variance over time (i.e., from PD treatment session to session)—and, more particularly, a rate of change of counts over time (or "critical slope')—exceeds a selected amount. Again, such an alert can be in the form of a visible and/or audible signal to the patient 16, health-care worker, or otherwise; a hardware or other interrupt to system 12 of which test apparatus 42 forms a part; a software function call to such system; or otherwise.

As will be appreciated, an advantage of taking histograms from multiple CCD images is that it tends to emphasize intensity counts in the critical range. This improves the signal-to-noise ratio and, thereby, increases the efficacy of detection (e.g., of peritonitis or other conditions reflected by the effluent). In embodiments of the invention using this approach, the CCD 68 can be controlled (e.g., by the microprocessor 62 or otherwise) to acquire those multiple images during PD solution drainage by successively entering "acquisition" and "read" modes: the former, for acquiring images of the illuminated chamber 48; and the latter for reading those images to the microprocessor.

In other embodiments of the invention, the microprocessor can perform image pre-processing prior to taking the histograms. Thus, for example, it can eliminate pixel values representing scattering from effluent components that are too long (e.g., fibrin) or too short (e.g., RBCs)—both, by way of example, with respect to embodiments intended to count WBCs for purposes of peritonitis detection. Further such preprocessing may be selected depending upon the specifics of the application to which the invention is applied.

Described and shown herein are apparatus and methods for testing PD effluent meeting the objects set forth above. It will be appreciated that the embodiments described here are merely examples of the invention and that other embodiments, incorporating changes therein, fall within the scope of the invention. Thus, by way of non-limiting example, it will be appreciated that the apparatus and methods as described above for use in detecting peritonitis from PD effluent flow can be applied in detecting blood (RBCs), bubbles and other desirable or undesirable byproducts of CAPD, APD and so forth, all by way of non-limiting example. Further, it will be appreciated that such apparatus and methods can be applied in detecting bubbles and other byproducts of hemodialysis.

In view thereof, what we claim is:

1. An apparatus for testing peritoneal dialysis (PD) effluent in a flow path, comprising
  A. an illumination source that illuminates peritoneal effluent in the flow path;
  B. a detector that (i) detects an illuminant any of reflected and scattered (hereinafter, collectively, "scattered") by the effluent, and (ii) includes a lens that resolves the scattered illuminant at a cellular scale of resolution such that separate cellular-sized components of a same type are distinguished from one another, where those components are any of white blood cells, red blood cells, fibrin, bubbles, and other cellular-sized components of the fluid, wherein
    the detector detects the scattered illuminant at a cellular scale of resolution such that said separate cellular-sized components of the same type in the effluent are (a) distinguished from one another based on an intensity and/or location of illuminant that is scattered therefrom and that is resolved by the lens, and (b) counted, and wherein the number of counts are analyzed over time and/or from a baseline to signal the onset of peritonitis.

2. The apparatus according to claim 1, in which the detector detects illuminant scattered from separate white blood cells (WBCs) in the effluent such that said WBCs are distinguished from one another.

3. The apparatus according to claim 2, wherein the detector counts WBCs in the effluent based on the intensity and/or location of illuminant scattered therefrom.

4. The apparatus according to claim 3, wherein the detector signals an onset of peritonitis if said counts change over time and/or vary from a baseline.

5. The apparatus according to claim 4, wherein said baseline is a baseline previously established for a patient from which the PD effluent is drained.

6. The apparatus according to claim 1, in which the detector detects illuminant scattered from cellular-sized components of different types in the effluent such that said components are distinguished from one another.

7. The apparatus according to claim 6, in which the detector detects illuminant scattered from white blood cells (WBCs) in the effluent such that they are distinguished from red blood cells (RBCs), fibrin and/or other components from which illuminant is scattered in the effluent.

8. An apparatus for testing peritoneal dialysis (PD) effluent in a flow path, comprising
  A. an illumination source that illuminates peritoneal effluent in the flow path;
  B. a detector that (i) detects an illuminant any of reflected and scattered (hereinafter, collectively, "scattered") by the effluent, and (ii) includes a lens that resolves the scattered illuminant at a cellular scale of resolution such that separate cellular-sized components of a same type are distinguished from one another, where those components are any of white blood cells, red blood cells, fibrin, bubbles, and other cellular-sized components of the fluid, the detector detecting the scattered illuminant at a cellular scale of resolution such that said separate cellular-sized components of the same type in the effluent are (a) distinguished from one another based on the intensity and/or location of illuminant that is scattered therefrom and that is detected by the lens, and (b) counted, wherein
    the detector signals an onset of peritonitis based on variance, over time and/or from a baseline, in counts of at least selected reflections and/or scatterings (hereinafter, collectively, "scatterings") detected thereby from components in the effluent.

9. The apparatus according to claim 8, wherein the detector determines a trend over time of variance of said counts.

10. The apparatus according to claim 9, wherein the detector determines the trend with respect to counts of white blood cells (WBCs) from which scatterings are detected.

11. The apparatus according to claim 9, wherein the detector determines a slope of a curve of said counts with respect to time.

12. The apparatus according to claim 11, wherein the detector signals an onset of peritonitis when said slope exceeds a selected amount.

13. The apparatus according to claim 8, wherein the detector counts illuminant scattering events occurring with respect to the effluent based on intensity and/or location of those scattering events.

14. An apparatus for testing peritoneal dialysis (PD) effluent in a flow path, comprising
  A. a laser that illuminates peritoneal effluent in the flow path; and
  B. a detector including (a) a lens that resolves illuminant any of reflected and scattered (hereinafter, collectively, "scattered") from components of the effluent at a cellular scale of resolution such that separate cellular-sized components of a same type are distinguished from one another, where those components are any of white blood cells, red blood cells, fibrin, bubbles, and other cellular-sized components of the fluid and (b) a pin-diode configured to detect and signal the occurrence of scattered illuminant such that said separate cellular-sized components of the same type in the effluent are counted and wherein the number of counts are analyzed over time and/or from a baseline to signal the onset of peritonitis.

15. The apparatus according to claim 14, in which the pin-diode detects scattering events detectable within a field of view perpendicular to a ray of illuminant sourced by the laser.

16. The apparatus according to claim 14, in which the laser generates a beam of illuminant that is positioned within a portion of the flow path from which scattering events are detected by the pin-diode.

17. The apparatus according to claim 16, in which the beam is substantially centered within the portion of the flow path from which scattering events are detected by the pin-diode.

18. The apparatus according to claim 16, in which the beam has a width selected in accord with size characteristics of the components from which scattering events are to be detected by the pin-diode.

19. The apparatus according to claim 16, in which the beam has any of a circular and gaussian cross-section.

20. The apparatus according to claim 14, where the detector counts at least selected reflections and/or scatterings (hereinafter, collectively, "scatterings") signaled by the pin-diode from components in the effluent.

21. The apparatus according to claim 14, wherein the detector signals an onset of peritonitis based on variance, over time and/or from a baseline, in counts of at least selected scatterings signaled by the pin-diode.

22. The apparatus according to claim 21, wherein the detector determines a trend over time of variance of said counts.

23. The apparatus according to claim 22, wherein the detector determines the trend with respect to counts of white blood cells (WBCs) from which scatterings are detected.

24. The apparatus according to claim 22, wherein the detector determines a slope of a curve of said counts with respect to time.

25. The apparatus according to claim 24, wherein the detector signals an onset of peritonitis when that slope exceeds a selected amount.

26. The apparatus according to claim 14, wherein the pin-diode signals illuminant scattered from separate white blood cells (WBCs) in the effluent such that those WBCs are distinguished from one another.

27. The apparatus according to claim 26, wherein the detector counts WBCs in the effluent based on the intensity and/or location of illuminant scattered therefrom.

28. The apparatus according to claim 27, wherein the detector signals the onset of peritonitis if said counts change over time and/or vary from a baseline.

29. The apparatus according to claim 28, wherein said baseline is a baseline previously established for a patient from which the PD effluent is drained.

30. The apparatus according to claim 14, in which the pin-diode signals illuminant scattered from cellular-sized components of different types in the effluent such that said components are distinguished from one another.

31. The apparatus according to claim 30, in which the pin-diode signals illuminant scattered from WBCs in the effluent such that they are distinguished from red blood cells (RBCs), fibrin and/or other components from which illuminant is scattered in the effluent.

32. An apparatus for testing peritoneal dialysis (PD) effluent in a flow path, comprising
  A. an illumination source that illuminates peritoneal effluent in the flow path; and
  B. a detector including (a) a lens that resolves illuminant any of reflected and scattered (hereinafter, collectively, "scattered") from components of the effluent at a cellular scale of resolution such that separate cellular-sized components of a same type are distinguished from one another, where those components are any of white blood cells, red blood cells, fibrin, bubbles, and other cellular-sized components of the fluid and (b) a charge-coupled device (CCD) configured to image the scattered illuminant such that said separate cellular-sized components of the same type in the effluent are (a) distinguished from one another based on the intensity and/or location of illuminant that is scattered therefrom and (b)-counted, wherein the number of counts are analyzed over time and/or from a baseline to signal the onset of peritonitis.

33. The apparatus according to claim 32, wherein the detector generates a histogram of one or more such images.

34. The apparatus according to claim 33, wherein the detector counts scattering events based on intensities imaged by the CCD.

35. The apparatus according to claim 34, wherein the detector generates the histogram from multiple images taken from drainage of spent PD solution from a patient.

36. The apparatus according to claim 32, wherein the illumination source is a laser diode.

37. The apparatus according to claim 36, in which the CCD detects scattering events detectable within a field of view perpendicular to a ray of illuminant sourced by the laser diode.

38. The apparatus according to claim 36, in which the laser diode generates a beam of illuminant disposed within a portion of the flow path from which scattering events are detected by the CCD.

39. The apparatus according to claim 38, in which the beam is substantially centered within the portion of the flow path from which scattering events are detected by the CCD.

40. The apparatus according to claim 38, in which the beam has a width selected in accord with size characteristics of the components from which scattering events are to be detected by the CCD.

41. The apparatus according to claim 38, in which the beam has any of a circular and gaussian cross-section.

42. The apparatus according to claim 32, in which the CCD images illuminant scattered from separate white blood cells (WBCs) in the effluent such that said WBCs are distinguished from one another.

43. The apparatus according to claim 42, wherein the detector counts WBCs in the effluent based on the intensity and/or location of illuminant scattered therefrom.

44. The apparatus according to claim 43, wherein the detector signals an onset of peritonitis if said counts change over time and/or vary from a baseline.

45. The apparatus according to claim 44, wherein said baseline is a baseline previously established for a patient from which the PD effluent is drained.

46. The apparatus according to claim 32, in which the CCD images illuminant scattered from cellular-sized components of different types in the effluent such that said components are distinguished from one another.

47. The apparatus according to claim 46, in which the detector images illuminant scattered from white blood cells (WBCs) in the effluent such that they are distinguished from red blood cells (RBCs), fibrin and/or other components from which illuminant is scattered in the effluent.

48. The apparatus according to claim 32, wherein the detector signals an onset of peritonitis based on variance, over time and/or from a baseline, in counts of at least selected reflections and/or scatterings (collectively, "scatterings") imaged by the CCD from components in the effluent.

49. The apparatus according to claim 48, wherein the detector determines a trend over time of variance of said counts.

50. The apparatus according to claim 49, wherein the detector determines the trend with respect to counts of white blood cells (WBCs) from which scatterings are imaged.

51. The apparatus according to claim 48, wherein the detector determines a slope of a curve of said counts with respect to time.

52. The apparatus according to claim 51, wherein the detector signals the onset of peritonitis when that slope exceeds a selected amount.

53. A device for automated peritoneal dialysis comprising the apparatus of any of claims 1, 8, 14 and 32 in a flow path of peritoneal dialysis (PD) effluent produced by such device.

54. A method for testing peritoneal dialysis (PD) effluent in a flow path, comprising
  A. illuminating peritoneal effluent in the flow path;
  B. detecting, with at least a lens, illuminant any of reflected and scattered (hereinafter, collectively "scattered") by the effluent at a cellular scale of resolution such that separate cellular-sized components of a same type in the effluent are (a) distinguished from one another based on the intensity and/or location of illuminant that is scattered therefrom, and (b) counted, where the components are any of white blood cells, red blood cells, fibrin, bubbles, and other cellular-sized components of the fluid, and wherein the number of counts are analyzed over time and/or from a baseline to signal the onset of peritonitis.

55. The method according to claim 54, comprising detecting illuminant scattered from separate white blood cells (WBCs) in the effluent such that said WBCs are distinguished from one another.

56. The method according to claim 55, comprising counting WBCs in the effluent based on the intensity and/or location of illuminant scattered therefrom.

57. The method according to claim 56, comprising signaling an onset of peritonitis if said counts change over time and/or vary from a baseline.

58. The method according to claim 54, comprising detecting illuminant scattered from cellular-sized components of different types in the effluent such that said components are distinguished from one another.

59. The method according to claim 58, comprising detecting illuminant scattered from white blood cells (WBCs) in the effluent such that they are distinguished from red blood cells (RBCs), fibrin and/or other components from which illuminant is scattered in the effluent.

60. An apparatus for testing dialysis effluent in a flow path, comprising
  A. an illumination source that illuminates effluent in the flow path;
  B. a detector that includes a lens that resolves illuminant scattered from components of the effluent at a cellular scale of resolution, wherein
    the detector detects the scattered illuminant at a cellular scale of resolution such that separate cellular-sized components of a same type in the effluent are (a) distinguished from one another based on the intensity and/or location of illuminant that is scattered therefrom and that is detected by the detector and (b) counted, where those components are any of white blood cells, red blood cells, fibrin, bubbles, and other cellular-sized components of the fluid and wherein the number of counts are analyzed over time and/or from a baseline to signal the onset of peritonitis.

61. A method for testing effluent in a flow path, comprising
  A. illuminating effluent in the flow path;
  B. detecting, with at least a lens that resolves illuminant scattered from components of the effluent at a cellular scale of resolution, illuminant any of reflected and scattered (hereinafter, collectively, "scattered") by the effluent at a cellular scale of resolution such that at least selected separate cellular-sized components of a same type in the effluent are (a) distinguished from one another based on the intensity and/or location of illuminant that is scattered therefrom, and (b) counted, where those components are any of white blood cells, red blood cells, fibrin, bubbles, and other cellular-sized components of the fluid and wherein the number of counts are analyzed over time and/or from a baseline to signal the onset of peritonitis.

* * * * *